United States Patent [19]

Tepic

[11] Patent Number: 5,024,618
[45] Date of Patent: Jun. 18, 1991

[54] EXTERNAL FIXATION DEVICE

[75] Inventor: Slobodan Tepic, Davos, Switzerland

[73] Assignee: Synthes U.S.A., Paoli, Pa.

[21] Appl. No.: 465,575

[22] Filed: Jan. 18, 1990

Related U.S. Application Data

[63] Continuation of Ser. No. 184,802, Apr. 22, 1988, abandoned.

[30] Foreign Application Priority Data

Apr. 30, 1987 [WO] PCT Int'l
Appl. ............... PCT/EP87/00235

[51] Int. Cl.⁵ .................................................. A61F 5/04
[52] U.S. Cl. ........................................ 606/53; 606/54; 606/59
[58] Field of Search ................................. 606/54–59, 606/53

[56] References Cited

U.S. PATENT DOCUMENTS

| | | | |
|---|---|---|---|
| 1,789,060 | 1/1931 | Weisenbach | 606/54 |
| 2,435,850 | 2/1948 | Siebrandt | 606/54 |
| 3,985,127 | 10/1976 | Volkov | 606/56 |
| 4,185,623 | 1/1980 | Volkov | 606/56 |
| 4,273,116 | 6/1981 | Chiquet | 606/54 |
| 4,393,868 | 7/1983 | Teague | 606/54 |
| 4,584,995 | 4/1986 | Koeneman | 606/54 |
| 4,757,809 | 7/1988 | Koeneman | 606/59 |
| 4,768,524 | 9/1988 | Hardy | 606/54 |

FOREIGN PATENT DOCUMENTS

| | | | |
|---|---|---|---|
| 1569090 | 4/1969 | France. | |
| 347495 | 4/1931 | United Kingdom | 128/927 ZW |

OTHER PUBLICATIONS

"Journal of Bore & Joint Sugey" Oct. 1935 p. 1060 Roy R. Schubert, M.D.

Primary Examiner—Robert A. Hafer
Assistant Examiner—Michael Brown

[57] ABSTRACT

In an external fixation device for osteosynthesis, pins inserted into a bone are joined to a support rod by a clamp which leaves the end of the pin free to move in an arcuate direction under load, thus avoiding angulation of the pin in the bone and the resulting stress on the bone.

16 Claims, 12 Drawing Sheets

PRIOR ART

EXTERNAL FIXATION DEVICE

This is a continuation of co-pending application Ser. No. 184,802, filed on Apr. 22, 1988, now abandoned.

This invention relates to an external fixation device for osteosynthesis and in particular to a clamp for use in such a device which avoids undesirable stress on the bone being treated.

External fixation devices of the sort here involved employ pins which are passed through the bone fragments being joined. The butt or outer ends of the pins are fastened to a rod by clamps, and the pins, clamps and rod form a single frame which holds the bone fragments in the desired positions relative to each other.

Various proposals have been made for orthopedic external fracture fixation devices, so-called "external fixators" comprising a range of components which are variously connected with each other and with the fragments of a fractured bone by way of pins to form a support network holding the bone fragments in a desired relationship for the purposes of reunion.

The principle of external fixation entails load transfer from bone to an external frame by means of pins (or wires in the case of Ilizarov-type devices). The pins must be long enough to allow for clearing soft tissues covering the fractured bone, as well as for post-surgical treatment. The resulting distance between the treated bone and the external frame produces undesirable mechanical conditions at the pin-bone interface. Parametric analyses of stress concentrations for commonly used frame configurations have shown extremely high stress levels at the pin-bone interface. ("Parametric Analyses of Pin-Bone Stresses in External Fracture Fixation Devices", R. Huskes, E. Y. S. Chao, and T. E. Crippen, Journal of Orthopedic Research, Vol. 3, 341–349, 1985) Most of the stress concentration at pin-bone interface is produced by pin angulation within the cortices under functional loading and preloading. High stress levels at pin-bone interface are likely to contribute to, or even directly induce, pin loosening and the clinical complications that follow.

The invention provides a novel clamp for connecting the bone-pin with the supporting rod which lessens or eliminates angulation of the pin in the bone cortex, and thus avoids the drawbacks identified above. In a first aspect the invention provides a clamp for connecting a support rod to a bone pin comprising a first section, means for fixing the first section to a support rod, a second section, said second section being freely moveable in an arcuate path relative to said first section and means for connecting the butt or outer end of a bone pin to said second section. By making the outer end of the bone pin freely swingable or moveable in an arc, preferably the arc of a circle, whose radius is approximately the distance from the bone cortex to the butt end of the pin, it has proved possible to couple the reactive force exerted by the support rod against the clamp with the reactive moment between the pin and the rod so as to avoid angulation of the pin in the bone, thus avoiding the difficulties arising from such angulation.

The invention further comprises an external fixation device for use in osteosynthesis comprising a support rod, a bone pin for insertion into a bone and a clamp for connecting said pin to said rod, said clamp having a first section, means for attaching said rod to said first section, a second section, and means for attaching said second section to said pin, said second section being freely moveable in an arcuate path with respect to said first section.

The invention will be further described with reference to the accompanying drawings in which:

FIG. 11 is a schematic view partly in vertical section of a unilateral device according to the invention showing a coupled Referring first to FIG. 1, there is shown a fractured bone 1 supported in an external fixation device 100. In the device pins 3 are inserted through the fragments of the bone and are fixed to longitudinal rods 4 by means of clamps 5, there being one clamp for each pin. Transmission of a load (indicated as 6) on the bone is achieved in whole or in part through the device 100, i.e., through the pins 3, rods 4 and clamps 5 which make up a frame external to the bone.

Figure 1:
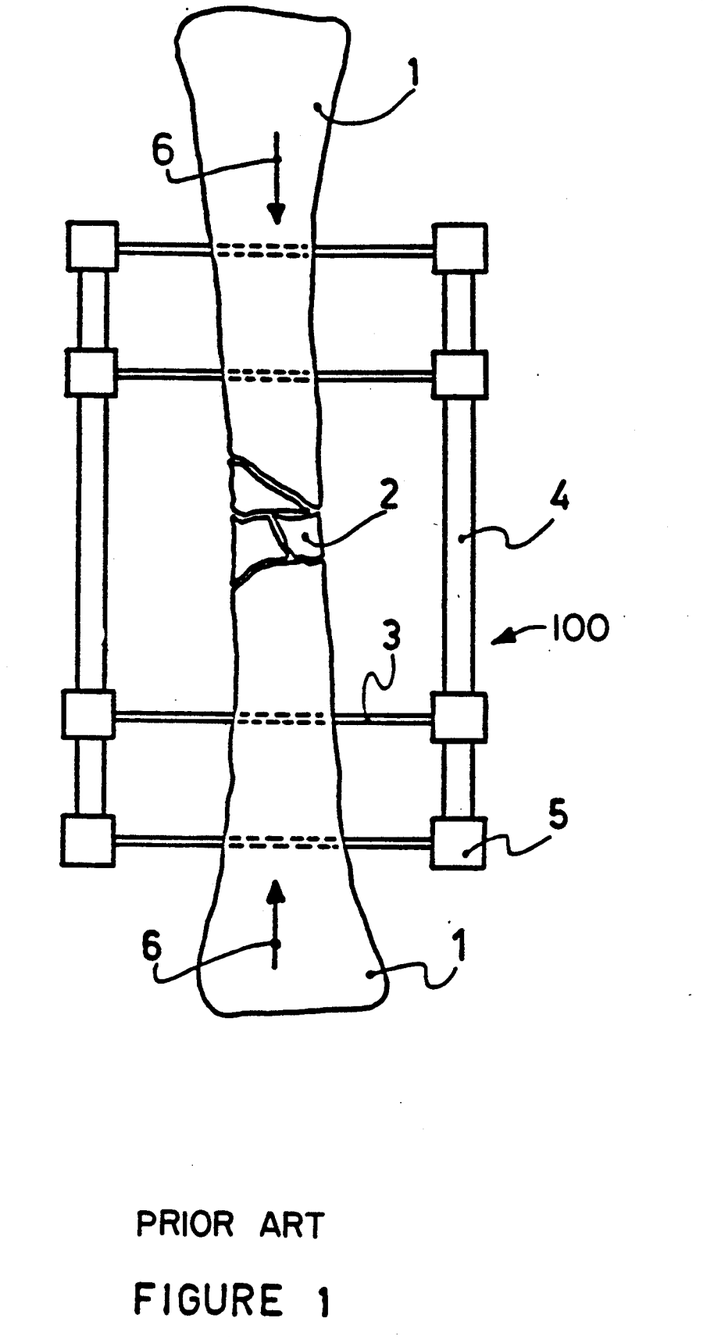
FIG. 1 is a schematic view of a prior art external fixation device applied to a fractured bone.
Figure 2:
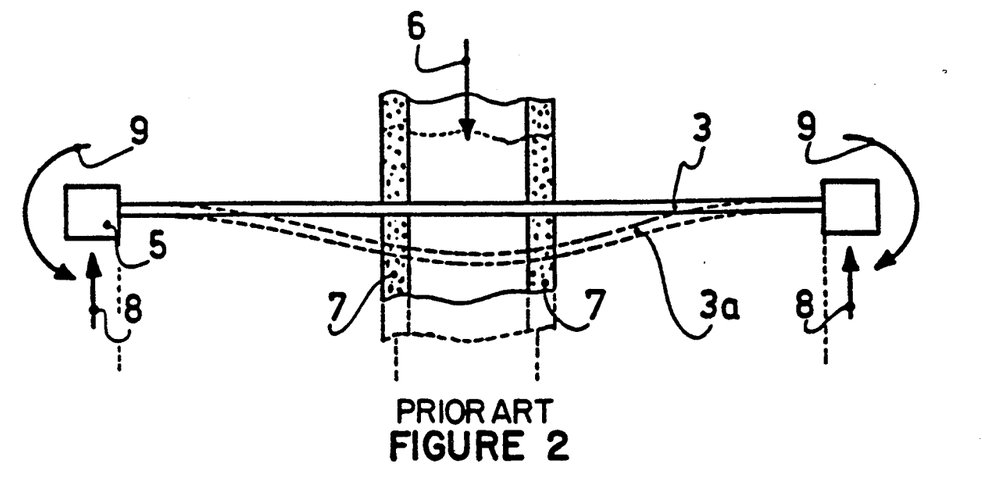
FIG. 2 is a schematic view of a bone under load showing the exaggerated form the pin deformation with the device of FIG. 1.
Figure 2A:
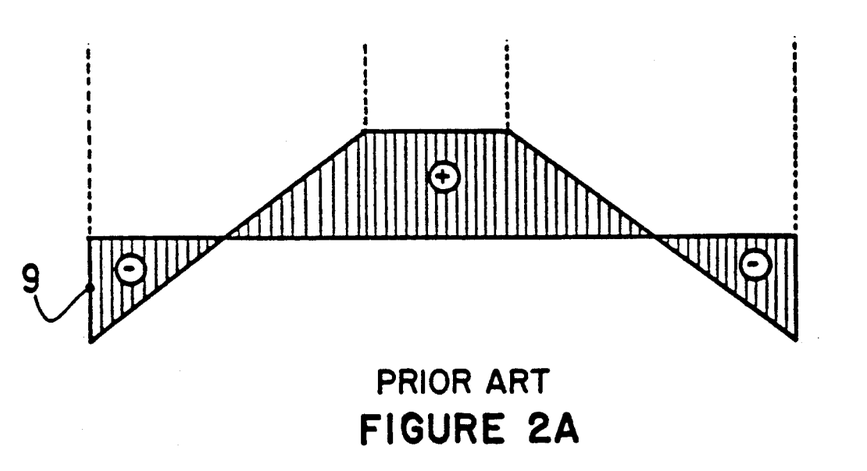
FIG. 2A is a diagram of the bending moments generated under the conditions of FIG. 2.

Under the load 6, in a conventional external fixation device, the pins 3 will deform in the pattern shown in FIG. 2. In FIG. 2 the shape of the pin under load is shown, exaggerated for illustration, in dashed lines at 3a. The reaction forces 8 exerted by the rod (4 in FIG. 1) against the pin 3 through clamps 5, which are rigidly fixed to the pin and rod, are in this bilateral frame, each equal to one half the axial load 6. The reactive moments 9 whose direction and relative magnitude are indicated in diagram of FIG. 2A will depend on the length of the pin and diameter of the bone. Between the bone cortices 7, the bending moment is constant.

Figure 3:
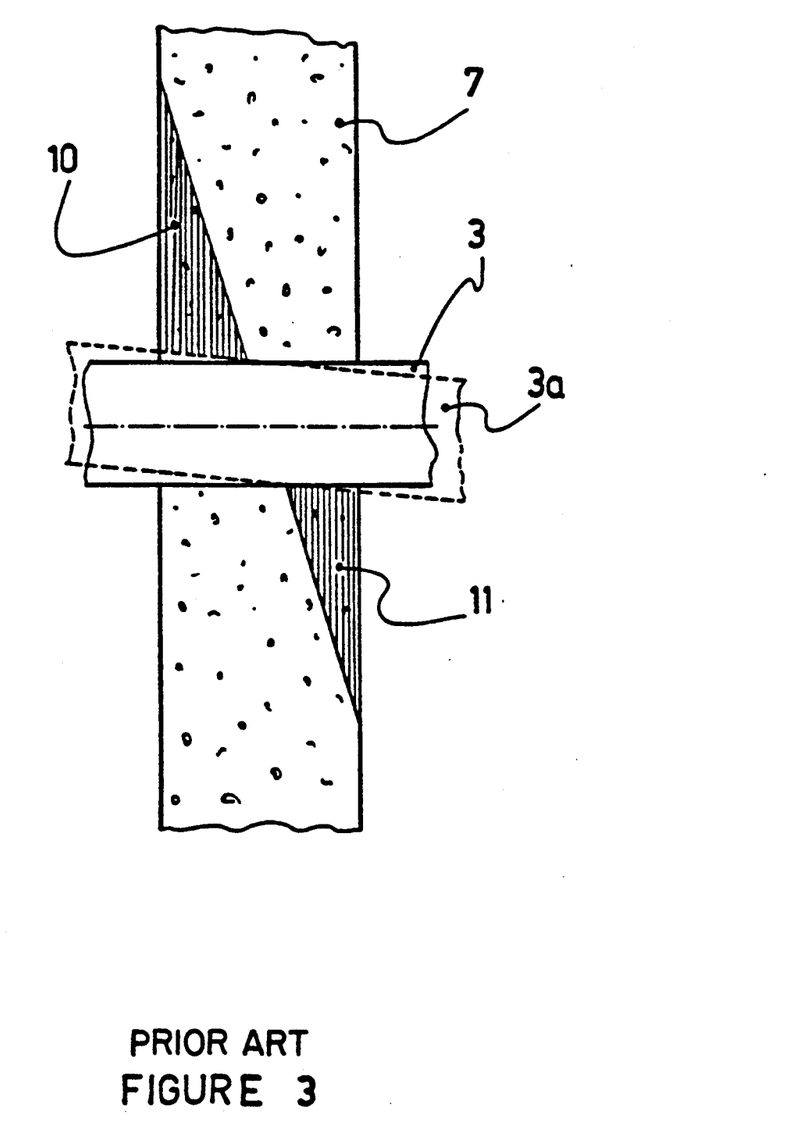
FIG. 3 is a schematic sectional view of the pin bone interface showing stress distribution in the bone under the conditions of FIG. 2.

With the pin 3 deformed as shown in FIG. 2, it tends to assume an angle, or angulate as it passes through the cortex on both sides of the bone, pressing against the cortex. This is illustrated in FIG. 3 where the stress distribution at the pinbone interfaces as the pin 3 passes through the cortex 7 is shown at 10, 11. The angular orientation of the pin is indicated at 3a.

Figure 4:
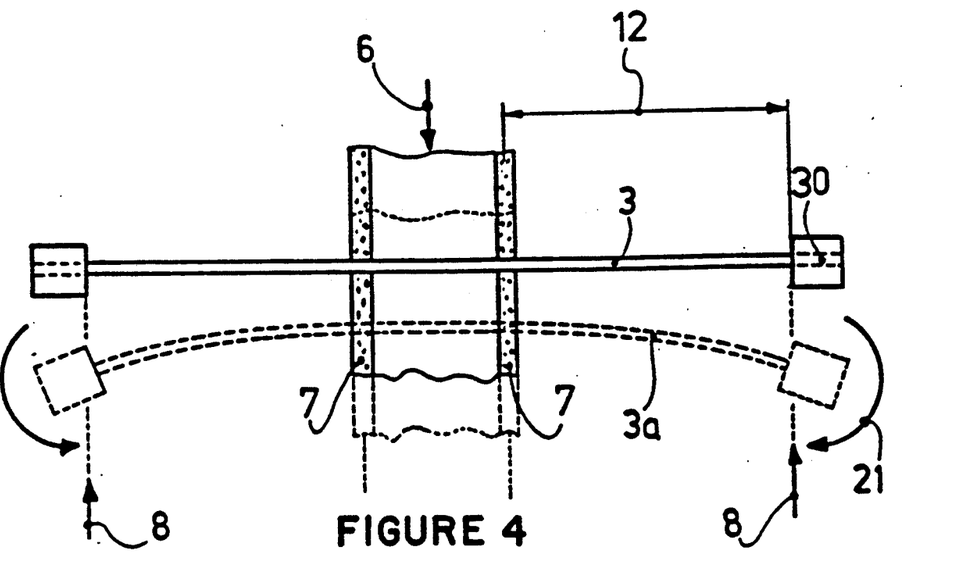
FIG. 4 is a schematic view of a bone under load showing in exaggerated form the pin deformation in a device according to the invention.
Figure 4A:
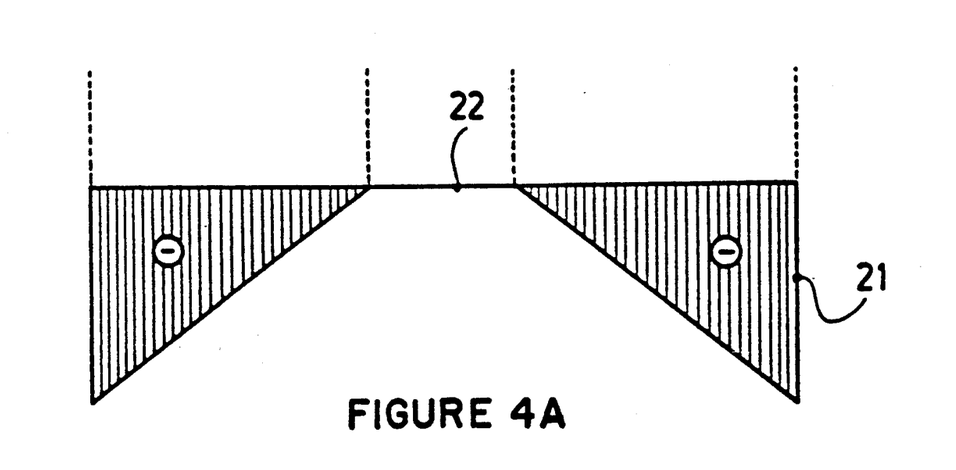
FIG. 4A is a diagram of the bending moments generated under the conditions of FIG. 4.

In accordance with the present invention, the clamps 5 are constructed so that the outer or butt ends of the pin 3 are permitted to move freely in an arcuate path when a load is applied to the bone. In FIG. 4, a pin 3 passes through a bone having cortices 7 and is secured to a support rod (not shown) via clamp 5, one at each end of the pin. In accordance with the invention, the clamps are made with the structures described below which enables the butt ends 30 of the pin and a portion of the associated clamp to move freely in an arcuate path. With this construction, when a force 6 is applied to the bone, the pin moves into the position shown in dashed lines at 3a (in an exaggerated manner for illustration), provided that reactive moments 21 are high enough to eliminate a bending moment 22 between the cortices 7. The magnitude of the movement 21 is the product of the reactive force 8 exerted by the support rod on the pin and the free pin length 12. The bending moments are illustrated graphically in FIG. 4A.

Figure 5:
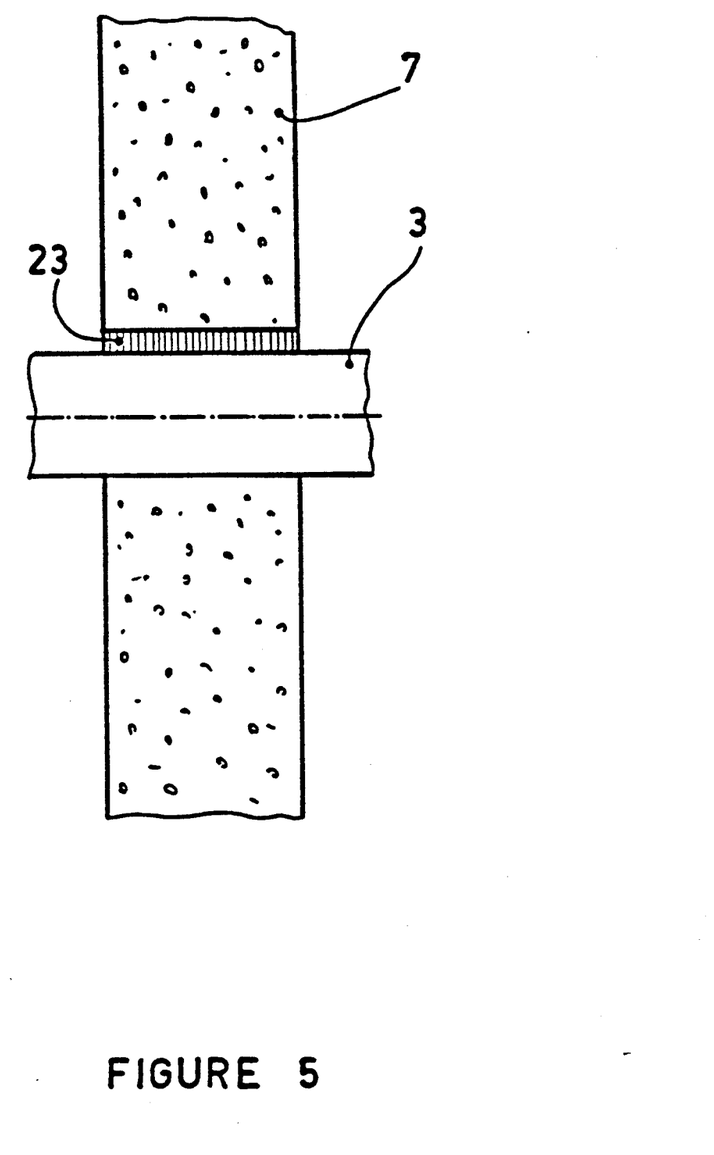
FIG. 5 is a diagrammatic sectional view showing the reduced stresses at the pin-bone interface under the conditions of FIG. 4.

Since in the case shown in FIG. 4 there is no bending moment between the cortices, there is no angulation of the pins, and the stress on the bone is uniform across the cortices, as shown in FIG. 5 where 23 represents the stress in cortex 7.

Figure 6:
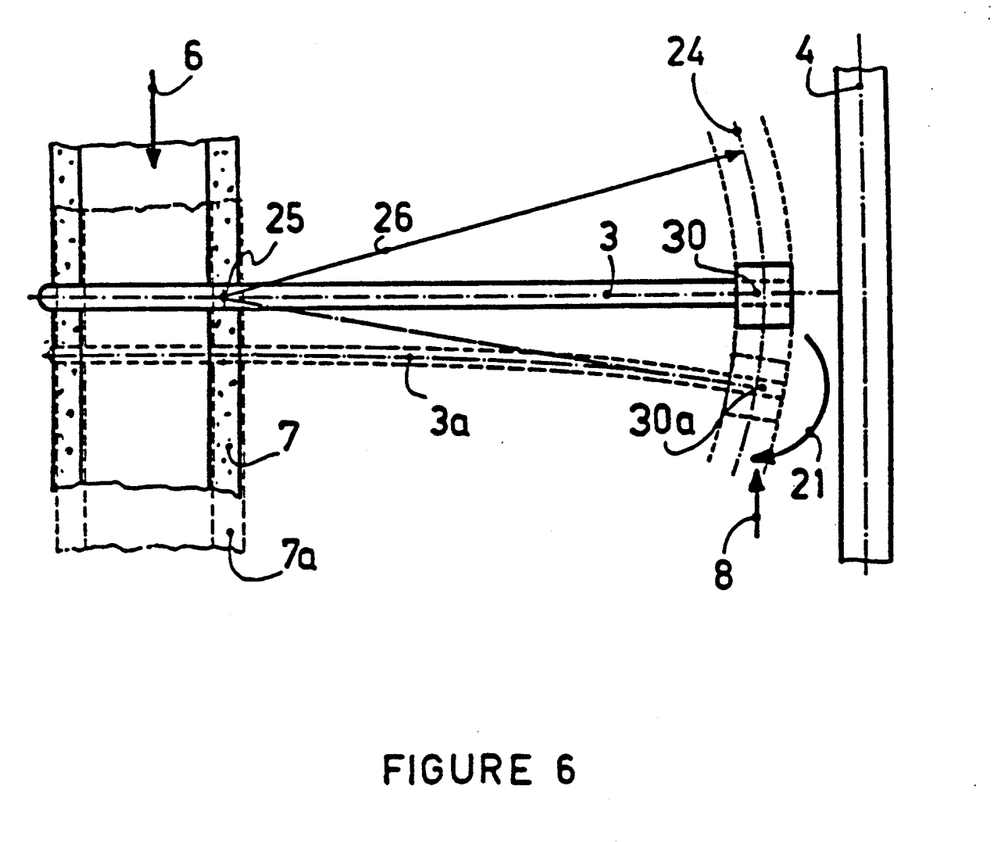
FIG. 6 is a schematic view partly in vertical section of a unilateral frame device according to the invention showing loads and deformations.

In FIG. 6 there is shown, via a schematic diagram of a unilateral fixation device, the kinematic constraint necessary to give the conditions illustrated in FIG. 4. Under load 6 the butt end 30 of pin 3 is free to move along the arc of a circle whose center 25 is within the near cortex 7 of bone 1. Under these conditions the reactive moment 21 will be equal to the product of the reactive force 8 exerted by the rod 4 against the pin multiplied by the radius 26 of the circle 24. Radius 26 is approximately equal to the free length 12 (FIG. 4) of the pins 3. The path or trajectory 24 of the butt end of the pin should remain fixed with relation to rod 4.

Figure 7:
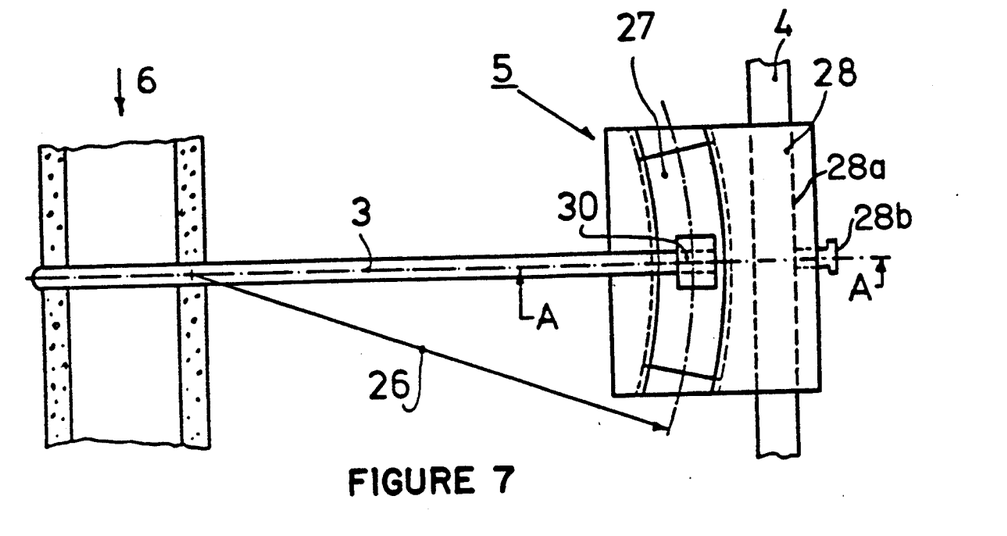
FIG. 7 is a schematic view partly in vertical section of a unilateral device according to the invention showing a clamp having a gliding construction.
Figure 7A:
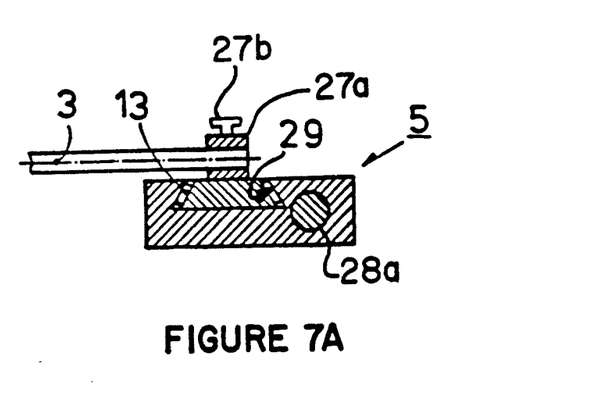
FIG. 7A is a horizontal cross-section, along the lines A..A of FIG. 7.

Turning to specific clamp structures suitable for providing the arcuate movement of the pin end described above, in FIG. 7 the clamp 5 comprises a block of metal plastic or other suitable material forming a first section or body 28 of the clamp. A hole 28a is provided for the rod 4. Holding means such as a set screw 28b are provided for attaching the clamp to the rod 4. In the body 28 there is a groove 29 formed as the arc of a circle whose radius 26 is optimally the distance from the near cortex of the bone 1 which is to be treated, to the free or butt end 30 of the pin. A glider or slide 27 is seated in the groove 29 so that it slides along the groove. Rollers 13 may be provided to reduce friction between the glider and the walls of the groove, so that when installed the end of the pin will have free movement. A bracket 27a is fixed to the top of the glider for receiving the butt end 30 of a single pin 3. Retaining means such as a set screw 27b may be used to fix the pin in the bracket. As indicated in FIG. 7, when a force 6 is applied to the bone the glider 27 will move downwardly along the arc of the circle and the pin will assume the configuration shown in FIG. 4.

Figure 8:
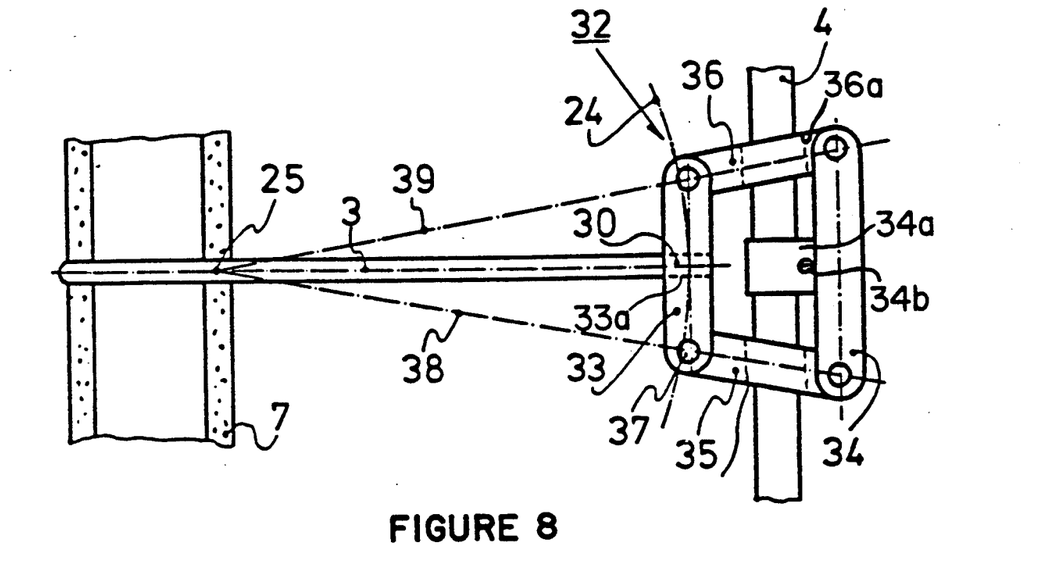
FIG. 8 is a schematic view partly in vertical section of a unilateral device according to the invention showing a clamp designed as a four-bar linkage.

In FIG. 8 the clamp takes the form of a four-bar linkage 32. This consists of an outer bar 34 which is fixed to the support rod 4 by bracket 34a and set screw 34b arranged to bear tangentially against the rod 4, and an inner bar 33. The inner bar 33 has a socket 33a for receiving a single pin 3 and may be retained in the socket by a frictional fit or by external means such as a set screw (not shown). The inner bar 33 is shorter than the outer bar 34. The inner and outer bars are connected by side bars 35, 36 which are joined by pivot pins 37 at their ends to the ends of bars 33, 34, to make the bar 33 freely swingable with respect to bar 34. The side bars 35, 36 have apertures 35a, 36a cut in their sides to permit side wise displacement of the side bars relative to rod 4 upon arcuate movement of the pin end 30. The center of arcuate movement of bar 33 with respect to bar 34 lies at the intersection 25 of the axes 38 and 39 of the side bars 35 and 36, which should be within the near cortex of bone 1. For small deformities, the butt end 30 of pin 3 will move in a trajectory 24 which will be approximately the arc of a circle having a radius equal to the distance from point 25 to the butt end 30 of the pin 3.

Figure 9:
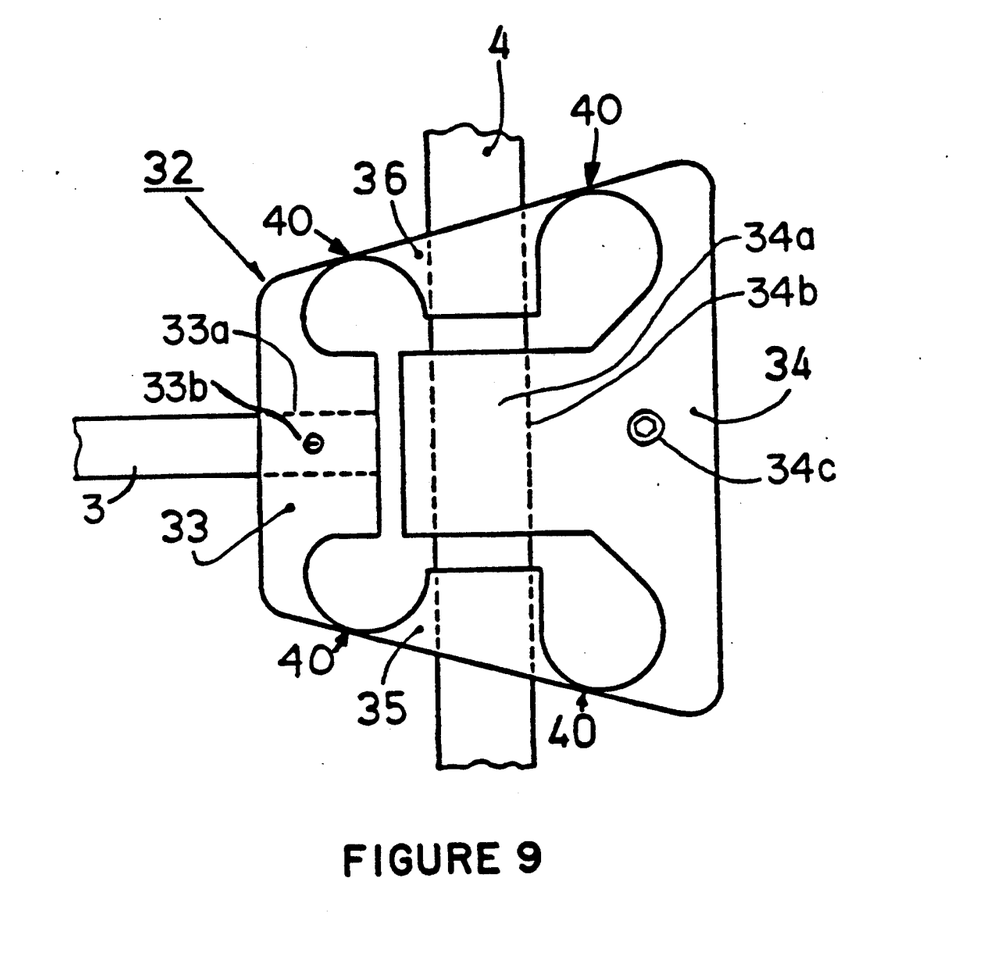
FIG. 9 is a schematic view of a unilateral device according to the invention showing a clamp designed as a unitary flexible four-bar linkage.
Figure 9A:
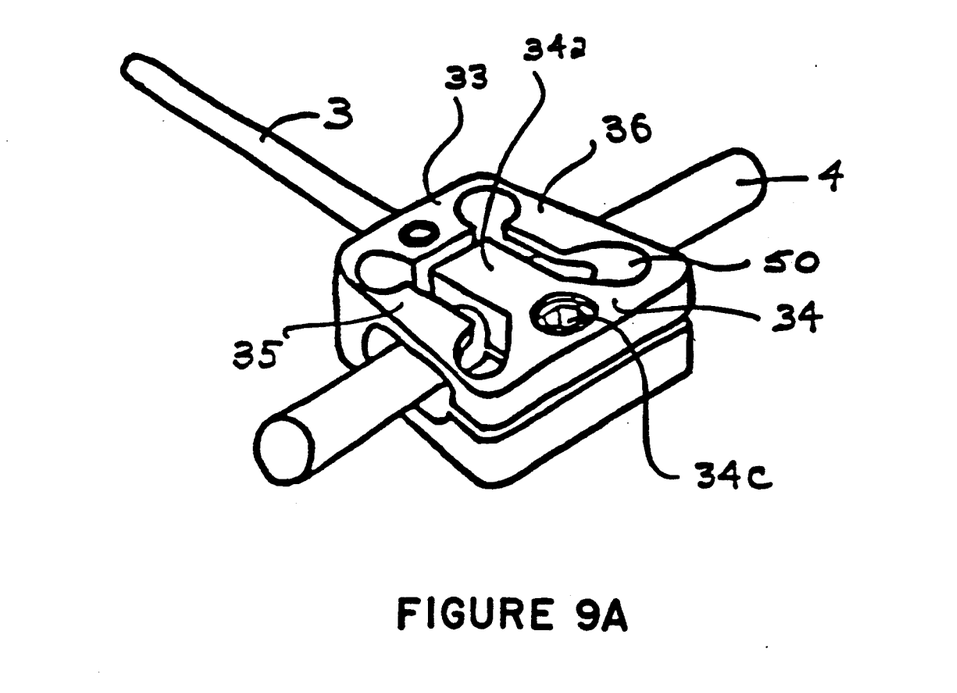
FIG. 9A is a schematic perspective view of the device of FIG. 9.

In FIGS. 9 and 9A there is shown a clamp 32 which functions similarly to the clamp of FIG. 8 but which may be made of a single piece of metal. In the clamp of FIGS. 9 and 9A there is an outer section 34 which is separated from an inner section 33 by a cut-out area 50. The section 34 is split into upper and lower parts as shown in FIG. 9A. It is fitted on rod 4 by a tang 34a which has an aperture 34b to accommodate the rod. A set screw 34c has a head which is seated in the upper part of section 34 and a threaded shank which is screwed into the lower part, thus enabling the device to be secured to the pin 4.

The inner section 33 has a socket 33a for receiving a pin 3. A set screw 33b may be used to retain the pin in the socket.

The sections 34 and 33 are connected by side sections 35 and 36, which at points 40 are sufficiently reduced in thickness to make them flexible. Thus the end of pin 3 is enabled to assume an arcuate movement by bending of the body 32 at points 40.

Figure 10:
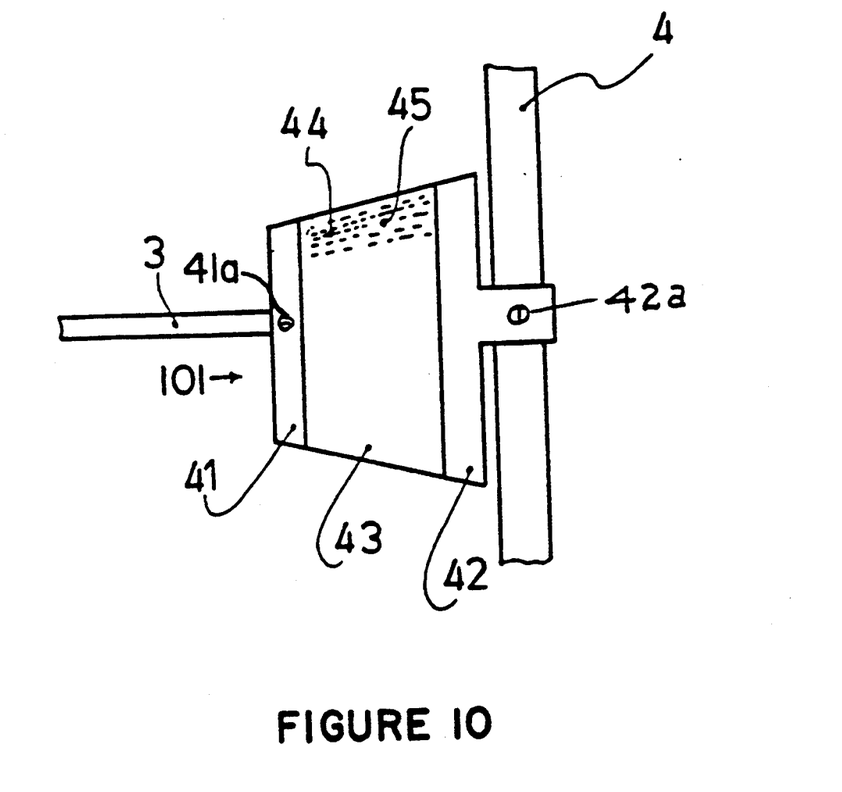
FIG. 10 is a schematic view of a unilateral device according to the invention showing a clamp made as a composite structure.

In FIG. 10 the clamp 101 comprises an outer 42 section clamped to the rod 4 via set screw 4a and an inner section 41 fixed to pin 3 via set screw 41a. Joining the two sections is a block 43 consisting of an elastomeric matrix 45, e.g., of natural or synthetic rubber, reinforced by fibers 44.

Figure 11:
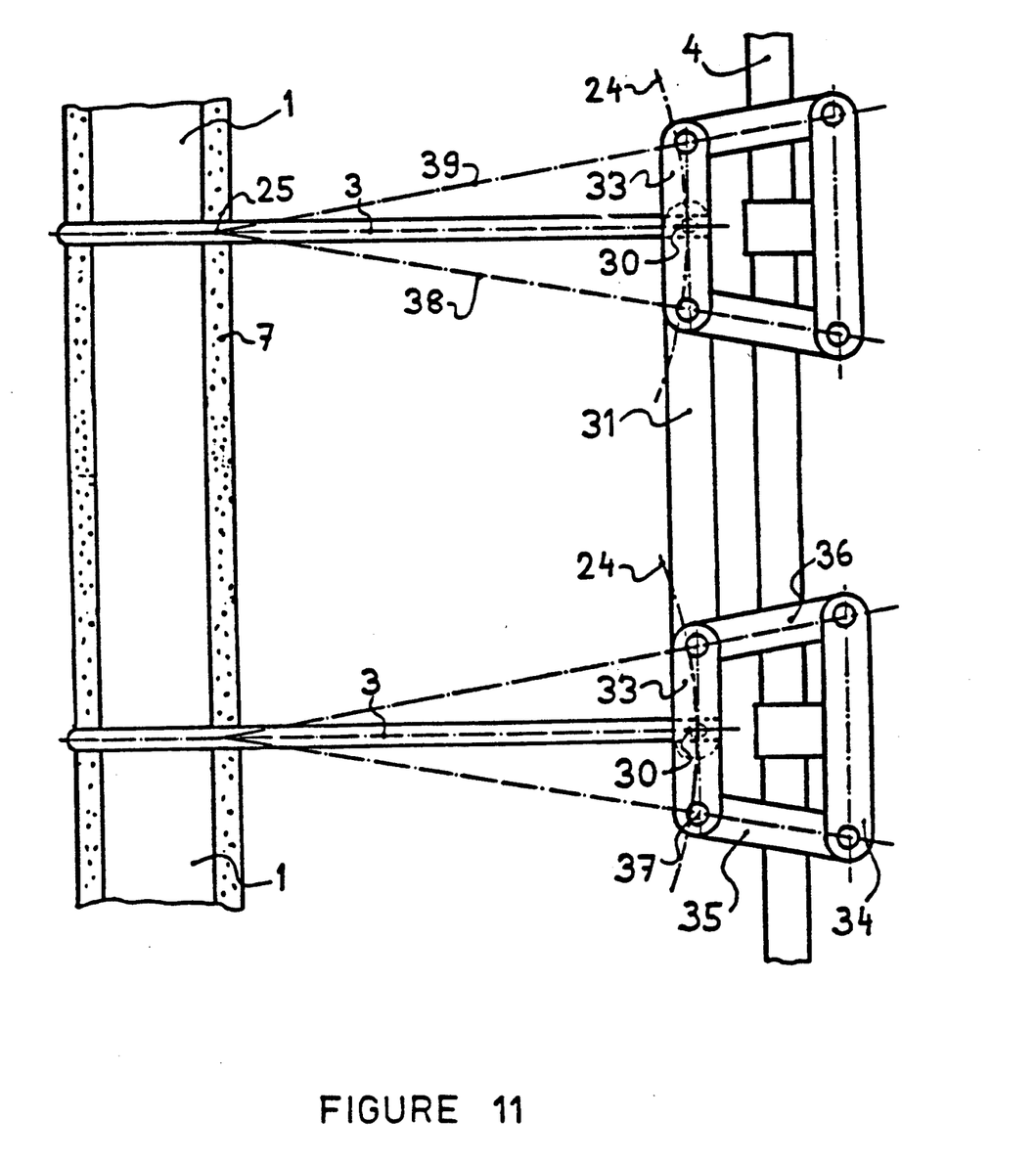

In the device shown in FIG. 11 two clamps of the type shown in FIG. 8 are employed on each side of the fracture. Under these circumstances an additional kinematic constraint is necessary to prevent rotation of the bones in the plane of the frame. This is achieved in the device shown in FIG. 11 by adding a bar link 31 which is pivotally pinned to the inner bars 33 at the points of connection of the bone pins 3.

Rotational stability in the bone-rod plane may also be achieved by the use of at least three pins per bone fragment. In that case additional constraint such as that realized with the bar link 31 would not be necessary.

It will be understood that although in FIGS. 8–11 the invention is described in connection with a unilateral frame and a single pin for simplicity, the invention is applicable to bilateral, or indeed multilateral, arrangements having a multiplicity of pins.

What is claimed is:

1. A clamp for connecting a support rod to a bone pin in the external fixation of fractured bones, said clamp comprising a first section, means for fixing said first section to a support rod, a second section, connecting means for connecting said second section to said first section, a single bone pin having a longitudinal axis, said bone pin being positioned in said second section, said connecting means constraining movement of said second section relative to said first section to an arcuate path which is symmetrical relative to said first section.

2. The clamp claimed in claim 1 wherein the second section is moveable in the arc of a circle.

3. The clamp claimed in claim 1 wherein the first section comprises a first bar, the second section comprises a second bar, generally parallel to the first bar and further comprising two side bars, each side bar being pivotally attached to the ends of the first and second bars.

4. The clamp claimed in claim 1 wherein the said first and second sections are connected by flexible connecting means.

5. A clamp for connecting a support rod to a bone pin in the external fixation of fractured bones, said clamp comprising a first section having an arcuate groove, means for attaching said first section to a support rod, a second section slidably positioned in said groove and a bone pin in said second section, said second section being capable of arcuate movement which is symmetrical with respect to said first section.

6. A clamp for connecting a support rod to a bone pin in the external fixation of fractured bones, said clamp comprising a first section, means for attaching said first section to a support rod, a second section, means for attaching the end of a bone pin to said second section and a block of fiber reinforced elastomeric material connecting said first and second sections whereby the end of said pin is capable of symmetrical arcuate movement relative to said rod.

7. An external fixation device for use in osteosynthesis comprising a support rod, a bone pin for insertion into a bone and a clamp for connecting said pin to said rod, said clamp having a first section, means for attaching said first section to said rod, a second section and means for attaching a single bone pin in said second section, said second section being freely moveable relative to said first section along the arc of a circle, in a path symmetrical with respect to said first section.

8. An external fixation device for osteosynthesis comprising a plurality of bone pins each having a forward end for insertion into a bone and a butt end, a support rod and a plurality of clamps, one for each bone pin, for attaching the butt ends of said pins to said rod, each of said clamps having a first section for attachment to said rod and a second section freely swingable with respect to said first section, and means for attaching the butt end of a single pin to said second section, whereby said butt end is capable of arcuate movement with respect to said rod in a path symmetrical with respect to said first section.

9. The device claimed in claim 8 wherein the clamp comprises a first section, means for attaching said first section to said rod, a second section, means for attaching said second section to the butt end of a pin and flexible elements connecting said first and second sections.

10. An external fixation device for osteosynthesis comprising a plurality of bone pins each having a forward end for insertion into a bone and a butt end, a support rod and a plurality of clamps for attaching the butt ends of the pins to the rod, each of said clamps having a first section for attachment to said rod, said first section having an arcuate groove, a second section slidably positioned in said groove and means for attaching the butt end of a pin to said second section, whereby the butt end of the pin is arcuately movable relative to said rod along a path symmetrical with respect to the first section.

11. An external fixation device for osteosynthesis comprising a plurality of bone pins each having a forward and a butt end, a support rod and a plurality of clamps for attaching the butt ends of the pins to the rod, each of said clamps comprising a first section for attaching to the rod, a second section for attachment to the butt end of a pin and a block of fiber reinforced elastomeric material joining said first and second sections, whereby the butt end of the pin is arcuately movable relative to the rod.

12. An external fixation device for use in osteosynthesis in the treatment of a fractured bone comprising a first bone pin for insertion into the bone, a second bone pin for insertion into the bone, a support rod, and first and second clamps for connecting said first and second pins and only said first and second pins, to said rod, each of said clamps having a first section secured to said rod and a second section secured to a pin, said second section being connected to said first section, and freely movable in an arcuate path relative to said first section and symmetrical with respect to said first section and means connecting the second sections of said first and second clamps.

13. In an external fixation device for the treatment of a fractured bone having at least one pin having a forward end inserted into the cortex of the bone on each side of the fracture and a butt end, a support rod and clamping means for attaching the butt ends of each of said bone pins to said rod, the improvement wherein said clamping means comprises a first section, means for attaching said first section to a support rod, a second section, said section being freely movable in an arcuate path relative to said first section, and means for attaching the butt end of a pin to said second section, there being one clamp for each pin in said device, the butt end of each of said pins being capable of arcuate movement symmetrical to the first section when a load is placed on said bone.

14. The external fixation device claimed in claim 13 wherein the arcuate movement of the butt end of said pin is the arc of a circle.

15. The external fixation device claimed in claim 14 wherein the center of the circle lies in the near cortex of the bone.

16. An external fixation device for osteosynthesis comprising a plurality of bone pins each having a forward end for insertion into a bone and a butt end, a support rod and a plurality of clamps, one for each bone pin, for attaching the butt ends of said pins to said rod, each of said clamps comprising a four bar linkage comprising a first bar, means for attaching said first bar to said rod in a position approximately parallel to the axis of said rod, a second bar shorter than said first bar, means for attaching the second bar to the butt end of a pin and two connecting bars, pivotally attached to the ends of said first and second bars.

* * * * *

UNITED STATES PATENT AND TRADEMARK OFFICE
CERTIFICATE OF CORRECTION

PATENT NO.  : 5,024,618
DATED       : June 18, 1991
INVENTOR(S) : Slobodan Tepic It is certified that error appears in the above—identified patent and that said Letters Patent is hereby corrected as shown below:

Col. 2, line 44, after "coupled" insert --pair of clamps.--.

Col. 3, line 2 "pinbone" should be --pin-bone--.

Claim 11, col. 6, lines 11 and 12, delete "attaching" and insert --attachment--.

Signed and Sealed this

Twenty-fourth Day of November, 1992

Attest:

DOUGLAS B. COMER

*Attesting Officer*    *Acting Commissioner of Patents and Trademarks*